United States Patent [19]

Hargreaves

[11] Patent Number: 4,508,721
[45] Date of Patent: Apr. 2, 1985

[54] PYRIDAZIN-3-ONE DERIVATIVES

[75] Inventor: Rodney B. Hargreaves, Poynton, England

[73] Assignee: Imperial Chemical Industries, PLC, England

[21] Appl. No.: 438,729

[22] Filed: Nov. 3, 1982

[30] Foreign Application Priority Data

Nov. 12, 1981 [GB] United Kingdom ............... 8134177

[51] Int. Cl.³ .................. C07D 237/06; A61K 31/50
[52] U.S. Cl. ................................. 514/252; 544/238; 544/239
[58] Field of Search ................... 544/238; 424/250

[56] References Cited

U.S. PATENT DOCUMENTS 4,298,609 11/1981 Lesher et al. ............... 544/238
4,304,777 12/1981 Lesher et al. ............... 544/238
4,346,221 8/1982 Lesher et al. ............... 544/238

Primary Examiner—Nicholas S. Rizzo
Attorney, Agent, or Firm—Cushman, Darby & Cushman

[57] ABSTRACT

Heterocyclic compounds of the formula:

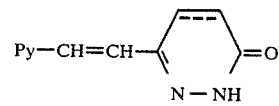

wherein the dotted line in the pyridazine nucleus indicates that a double bond is optional in this position, and wherein Py is a 2-, 3- or 4- pyridinyl group which is unsubstituted, or which bears one or two substituents selected from halogen, cyano, hydroxymethyl, carboxy, carbamoyl and alkyl, alkoxy, alkoxycarbonyl, alkylcarbamoyl and dialkylcarbamoyl wherein each alkyl or alkoxy has up to 4 carbon atoms, or which bears an oxygen substituent, either as an N-oxide or as an oxo substituent on the 2- or 4- carbon atom (that is, such as to form a pyridone); and acid-addition salts thereof; processes for their manufacture and pharmaceutical compositions containing them. The compounds possess cardiotonic and/or antihypertensive properties.

6 Claims, No Drawings

PYRIDAZIN-3-ONE DERIVATIVES

This invention relates to new heterocyclic compounds, some of which possess cardiotonic properties, some of which possess antihypertensive properties and some of which possess both said properties.

Many 6-aryl-dihydropyridazin-3-one derivatives are known which possess pharmaceutical properties affecting the cardiovascular system. These are described, for example, in the Journal of Medicinal Chemistry, 1974, 17, 273 $\propto$ 286 and in the Journal of Heterocyclic Chemistry, 1974, 11, 755–761, and there is much related patent literature.

A compound of considerable interest at present as a cardiotonic agent is a pyridone derivative known by the name AMRINONE, which has the structure:

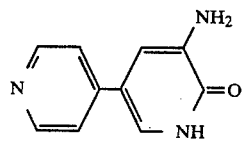

We have now found that certain pyridylvinyl-pyridazinone derivative possess valuable cardiotonic and/or antihypertensive properties.

According to the invention there is provided a heterocyclic compound of the formula:

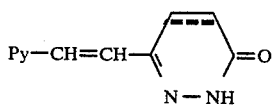

wherein the dotted line in the pyridazine nucleus indicates that a double bond is optional in this position, and wherein Py is a 2-, 3- or 4-pyridyl group which is unsubstituted, or which bears one or two substituents selected from halogen, cyano, hydroxymethyl, carboxy, carbamoyl and alkyl, alkoxy, alkoxycarbonyl, alkylcarbamoyl and dialkylcarbamoyl wherein each alkyl or alkoxy has up to 4 carbon atoms, or which bears an oxygen substituent, either as an N-oxide or as an oxo substituent on the 2- or 4-carbon atom (that is, such as to form a pyridone); or an acid-addition salt thereof.

A suitable alkyl, alkoxy, alkoxycarbonyl, alkylcarbamoyl or dialkylcarbamoyl substituent in the pyridine group is, for example, a methyl, ethyl, methoxy, ethoxy, methoxycarbonyl, ethoxycarbonyl, methylcarbamoyl, dimethylcarbamoyl or diethylcarbamoyl substituent.

A suitable acid-addition salt of the heterocyclic compound of the invention is, for example, a hydrochloride, hydrobromide, acetate, oxalate, tartrate or citrate.

Py is preferably unsubstituted 4-pyridyl.

Preferred heterocyclic compounds of the invention are 4,5-dihydro-6-($\beta$-pyrid-4-ylvinyl)pyridazin-3(2H)-one and 6-($\beta$-pyrid-4-ylvinyl)pyridazin-3(2H)-one, both of which possess valuable cardiotonic properties, and/or valuable antihypertensive properties.

A preferred process for the manufacture of a heterocyclic compound of the invention wherein the double bond in the pyridazine nucleus is absent comprises the reaction of a compound of the formula:

Py—CH=CH—COCH$_2$CH$_2$COOH where Py has the meaning stated above, with hydrazine.

The reaction is preferably carried out in a diluent or solvent, for example methanol, at laboratory temperature.

The starting material for the abovementioned reaction may be obtained by the reaction of an aldehyde of the formula Py—CHO wherein Py has the meaning stated above, with a keto-acid of the formula

CH$_3$COCH$_2$CH$_2$COOH

A compound wherein Py is an oxidised pyridyl group may be obtained by the oxidation, for example with a peroxide, of the corresponding unoxidised compound.

A compound wherein the pyridazine nucleus is fully unsaturated, that is, where the optional double bond is present, may be obtained by the dehydrogenation, for example with a sulphonyl chloride, of the corresponding partially saturated compound wherein said double bond is absent.

As stated above, some of the heterocyclic compounds of the invention possess cardiotonic activity. This may be demonstrated by their ability to increase the rate of change of aortic blood pressure in the anaesthetised cat. At a dose of the compound which produces an effective increase in said rate of change, that is, greater than a 25% increase, no symptom of toxicity is apparent.

As stated above, some of the heterocyclic compounds of the invention possess antihypertensive activity, as demonstrated by their ability to decrease the blood pressure of a normotensive cat or of a spontaneously hypertensive rat. The antihypertensive activity may also be demonstrated by the vasodilation effect produced by the heterocyclic compounds of the invention as shown by their ability to reduce spontaneous contraction in a rat portal vein preparation.

The heterocyclic compound of the invention may be administered to warm-blooded animals, including man, in the form of a pharmaceutical composition comprising as active ingredient at least one heterocyclic compound of the invention in association with a pharmaceutically acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the heterocyclic compound of the invention, one or more drugs selected from sedatives, for example phenobarbitone, meprobamate, chlorpromazine and benzodiazepine sedative drugs, for example chlordiazepoxide and diazepam; vasodilators, for example hydralazine, glyceryl trinitrate, pentaerythritol tetranitrate and isosorbide dinitrate; diuretics, for example chlorothiazide, hydrochlorothiazide, amiloride, bendrofluazide or chlorthalidone; $\beta$-adrenergic blocking agents, for example propranolol or atenolol; cardiac membrane stabilising agents, for example quinidine; agents used in the treatment of Parkinson's disease and other tremors, for example benzhexol; and cardiotonic agents, for example digitalis preparations.

When used for the treatment of acute or chronic heart failure, or of hypertension, in a warm-blooded animal, for example man, it is expected that the heterocyclic compound would be given to man at a total oral dose of between 100 mg. and 2000 mg. daily, at doses spaced at 6–8 hourly intervals, or at an intravenous dose of between 5 mg. and 100 mg.

Preferred oral dosage forms are tablets or capsules containing between 50 and 500 mg, and preferably 100 mg. or 500 mg., of active ingredient. Preferred intravenous dosage forms are sterile aqueous solutions of the heterocyclic compound containing between 0.05% and 1% w/w of active ingredient, and more particularly containing 0.1% w/v of active ingredient.

The invention is illustrated but not limited by the following Examples:

EXAMPLE 1

Hydrazine hydrate (0.67 ml.) was added to a stirred solution of 4-oxo-6-(4-pyridyl)hex-5-trans-enoic acid (2.5 g.) in methanol (150 ml.) and the mixture was stirred at laboratory temperature for 15 hours and then evaporated to dryness under reduced pressure. The residue was crystallised from methanol and there was thus obtained 4,5-dihydro-6-($\beta$-pyrid-4-yl-vinyl)pyridazin-3(2H)-one, m.p. 209°–211° C.

The hexenoic acid used as starting material was obtained as follows:

A solution of pyridine-4-aldehyde (26.75 g.), laevulinic acid (29 g.) and piperidine (10 ml.) in toluene (250 ml.) was heated under reflux in a Dean and Stark water-separating apparatus until 4.5 ml. of water had been separated, and was then cooled to 0° C. The toluene was decanted off and the residual syrup was stirred with acetone. The mixture was filtered and the residue was crystallised from methanol. There was thus obtained 4-oxo-6-(4-pyridyl)hex-5-trans-enoic acid, m.p. 218° C. (with decomposition).

The process described above was repeated using pyridine-3-aldehyde in place of pyridine-4-aldehyde. There was thus obtained as intermediate 4-oxo-6-(3-pyridyl)hex-5-trans-enoic acid, m.p. 184°–186° C., and as final product 4,5-dihydro-6-($\beta$-pyrid-3-ylvinyl)pyridazin-3(2H)-one, m.p. 210°–212° C.

EXAMPLE 2

Hydrogen peroxide (30 volumes; 1 ml.) was added to a mixture of 4,5-dihydro-6-($\beta$-pyrid-4-ylvinyl)pyridazin-3(2H)-one (1.0 g.) and glacial acetic acid (5 ml.) which was heated at 60° C., and the mixture was heated at 90° C. for 4 hours. Water (5 ml.) was added and the mixture was cooled and then concentrated to half-volume by evaporation. The addition of water, cooling and concentration were repeated until on cooling a solid precipitated. The mixture was filtered and the solid product was crystallised from methanol. There was thus obtained 4-$\beta$-(1,4,5,6-tetrahydro-6-oxopyridazin-3-yl)vinylpyridine-N-oxide, m.p. 266°–268° C. (with decomposition).

EXAMPLE 3 m-Nitrobenzenesulphonic acid (1.23 g.) was added to a stirred mixture of 4,5-dihydro-6-($\beta$-pyrid-4-ylvinyl)pyridazin-3(2H)-one (1.1 g.), sodium hydroxide (1.1 g.) and water (100 ml.) and the mixture was stirred at laboratory temperature for 2 hours, adjusted to pH7 with acetic acid and evaporated to dryness under reduced pressure. The residue was extracted with methanol and the methanolic solution was filtered and evaporated to dryness under reduced pressure. The residue was purified by chromatography on a silica gel column (180 g.) using a 9:1 v/v mixture of methylene chloride and methanol as eluant. The product was crystallised from methanol and there was thus obtained 6-($\beta$-pyrid-4-ylvinyl)pyridazin-3(2H)-one, m.p. 255°–257° C.

EXAMPLE 4

The process described in Example 1 was repeated using 6-methylpyridine-2-aldehyde in place of pyridine 4-aldehyde. There was thus obtained as intermediate 4-oxo-6-(6-methylpyrid-2-yl)hex-5-trans-enoic acid, m.p. 157°–158° C., and as final product 4,5-dihydro-6-($\beta$-6-methylpyrid-2-ylvinyl)pyridazin-3(2H)-one, m.p. 170°–171° C.

What we claim is:

1. A heterocyclic compound of the formula:

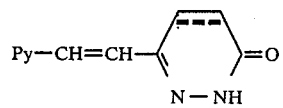

wherein the dotted line in the pyridazine nucleus indicates that a double bond is optional in this position, and wherein Py is a 4-pyridinyl group which is unsubstituted,
or an acid-addition salt thereof.

2. The compound 4,5-dihydro-6-($\beta$-4-pyridylvinyl)pyridazin-3(2H)one.

3. The compound 6-($\beta$-pyrid-4-ylvinyl)pyridazin-3(2H)-one.

4. A pharmaceutical composition having cardiotonic or antihypertensive active comprising as active ingredient at least one heterocyclic compound, claimed in claim 1, in association with a pharmaceutically acceptable diluent or carrier therefor.

5. A pharmaceutical composition as claimed in claim 4 which contains in addition to the heterocyclic compound one or more drugs selected from sedatives, vasodilators, $\beta$-adrenergic blocking agents, cardiac membrane stabilising agents, agents used in the treatment of Parkinson's disease and other tremors, and cardiotonic agents.

6. A method for the treatment of acute or chronic heart failure, or of hypertension, in a warm-blooded animal in need of such treatment, which comprises administering to said animal an effective amount of a heterocyclic compound claimed in claim 1.

* * * * *